United States Patent
Suppan et al.

(10) Patent No.: US 12,361,170 B2
(45) Date of Patent: Jul. 15, 2025

(54) METHOD AND SYSTEM FOR PROVIDING ANONYMIZED PATIENT DATASETS

(71) Applicant: Siemens Healthineers AG, Forchheim (DE)

(72) Inventors: Santiago Reinhard Suppan, Maxhuette-Haidhof (DE); Jorge Ricardo Cuellar Jaramillo, Baierbrunn (DE); Ute Rosenbaum, Kempten (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 251 days.

(21) Appl. No.: 17/873,384

(22) Filed: Jul. 26, 2022

(65) Prior Publication Data

US 2023/0045533 A1  Feb. 9, 2023

(30) Foreign Application Priority Data

Jul. 29, 2021 (DE) ............. 10 2021 208 233.5

(51) Int. Cl.
| | | |
|---|---|---|
| G06F 21/62 | (2013.01) | |
| G06F 18/23211 | (2023.01) | |
| G16H 50/20 | (2018.01) | |
| G16H 50/70 | (2018.01) | |

(52) U.S. Cl.
CPC .... *G06F 21/6254* (2013.01); *G06F 18/23211* (2023.01); *G16H 50/20* (2018.01); *G16H 50/70* (2018.01)

(58) Field of Classification Search
CPC .......... G06F 21/6254; G06F 18/23211; G16H 50/20; G16H 50/70; G16H 10/20; G16H 10/60
See application file for complete search history.

(56) References Cited

U.S. PATENT DOCUMENTS

| | | | | |
|---|---|---|---|---|
| 10,339,341 | B2* | 7/2019 | Mushkatblat | G06F 21/6245 |
| 11,380,441 | B1* | 7/2022 | Baker | H04L 67/52 |
| 2004/0257224 | A1* | 12/2004 | Sajkowsky | G07F 7/00 340/11.1 |
| 2014/0189858 | A1* | 7/2014 | Chen | G06F 21/6254 726/22 |

(Continued)

FOREIGN PATENT DOCUMENTS

WO  WO 2020234515 A1  11/2020

OTHER PUBLICATIONS

Majeed, Abdul, and Sungchang Lee. "Anonymization Techniques for Privacy Preserving Data Publishing: A Comprehensive Survey." IEEE access 9 (2021): 8512-8545. Web. (Year: 2021).*

(Continued)

*Primary Examiner* — Theodore C Parsons
*Assistant Examiner* — James P Moles
(74) *Attorney, Agent, or Firm* — Harness, Dickey & Pierce, P.L.C.

(57) ABSTRACT

A computer-implemented method for providing anonymized patient datasets, comprises: analyzing statistical population data to ascertain obfuscation parameters; and anonymizing patient datasets including quasi-identifiers as attributes by obfuscating the quasi-identifiers of the patient datasets based on the obfuscation parameters to generate the anonymized patient datasets. A system includes at least one processor and a memory, and is configured to provide the anonymized patient datasets.

20 Claims, 2 Drawing Sheets

(56) References Cited

U.S. PATENT DOCUMENTS

| | | | |
|---|---|---|---|
| 2014/0380489 A1* | 12/2014 | Hacid | G06F 21/6254 |
| | | | 726/26 |
| 2017/0083719 A1* | 3/2017 | Scaiano | H04L 63/0421 |
| 2018/0358112 A1* | 12/2018 | Sharifi Sedeh | G16H 10/60 |
| 2019/0272387 A1* | 9/2019 | Gkoulalas-Divanis | |
| | | | G06F 21/604 |
| 2020/0082120 A1* | 3/2020 | Richardson | G06F 21/604 |
| 2020/0265069 A1* | 8/2020 | Antonatos | G06F 21/6227 |
| 2021/0279219 A1* | 9/2021 | Fenton | G06F 16/221 |
| 2022/0050917 A1* | 2/2022 | Jiang | G06F 21/577 |
| 2022/0181023 A1* | 6/2022 | Mastoridis | G16H 10/60 |
| 2022/0237323 A1* | 7/2022 | Miettinen | G06F 21/6254 |
| 2022/0253554 A1* | 8/2022 | Goldsteen | G06F 21/6254 |
| 2022/0414262 A1* | 12/2022 | Degioanni | G06N 5/02 |
| 2023/0368870 A1* | 11/2023 | Hulsen | G16B 40/00 |

OTHER PUBLICATIONS

Springer-Link, van Tilborg H.C.A. et al.:"k-Anonymitiy", Encyclopedia of Cryptography and Security, https://link.springer.com/referenceworkentry/10.1007%2F978-1-4419-5906-5_754).
Wikipedia "k-anonymity", dated Jun. 9, 2021.

* cited by examiner

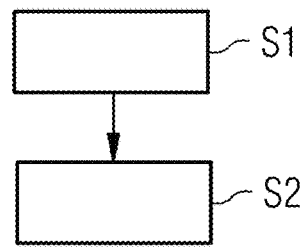
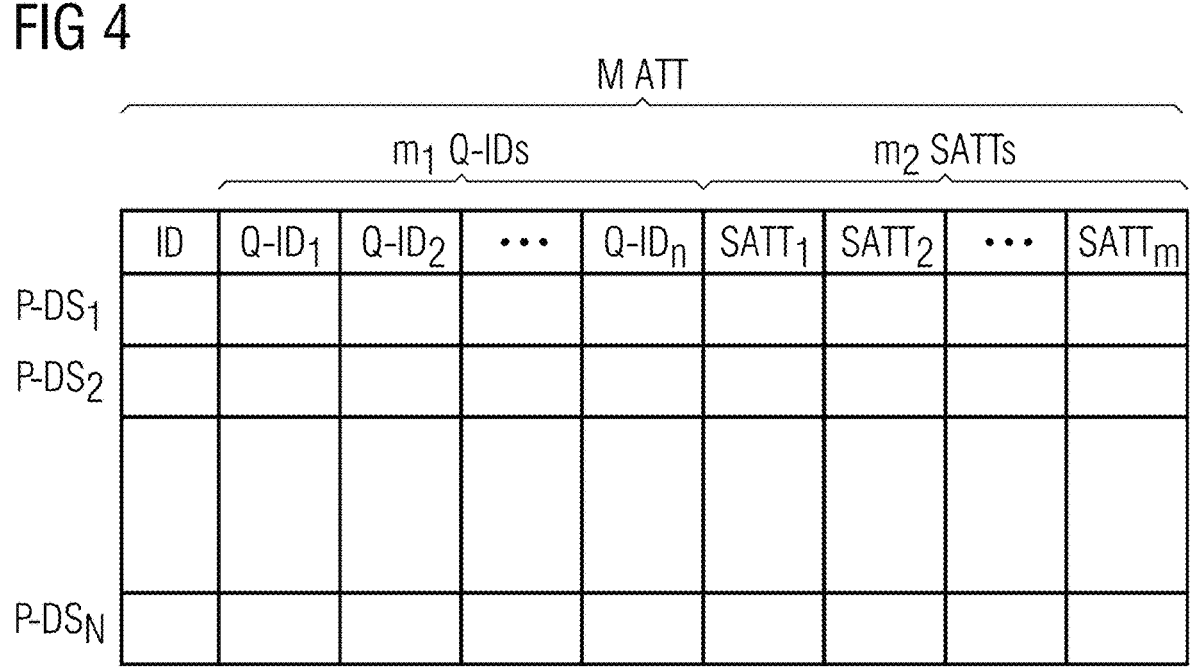

METHOD AND SYSTEM FOR PROVIDING ANONYMIZED PATIENT DATASETS

CROSS-REFERENCE TO RELATED APPLICATION(S)

The present application claims priority under 35 U.S.C. § 119 to German Patent Application No. 10 2021 208 233.5, filed Jul. 29, 2021, the entire contents of which are incorporated herein by reference.

FIELD

One or more example embodiments of the present invention relate to a computer-implemented method and to a corresponding system for providing patient datasets in digital form, which can be used, for example, for setting parameters of medical devices and/or for training artificial intelligence modules of medical devices.

BACKGROUND

Structured datasets are used in a large number of clinical applications and systems. These datasets relate to patients or people for whom case studies exist. A project can comprise, for example, different medical studies, which relate to a particular topic or to a particular medical situation. The medical studies can be carried out by different medical institutes. These medical institutes have, for example, hospitals, research institutes or laboratories. A medical study has, as a rule, a high number of case studies of patients. A project can therefore comprise a very high number of case studies with corresponding patient datasets. A project normally relates to a particular medical situation such as cardiac infarction or enlarged prostate. The large number of structured datasets of a project can be stored for further evaluation in a central database or in distributed databases. Patient data contains sensitive personal data, in particular health data, which has to be anonymized for further evaluation in order to guarantee the anonymity of the relevant patient. In the process the situation should be prevented where individual datasets can be isolated, which allow the respective patient or the respective person to be identified. Furthermore, it should be guaranteed that two different datasets, relating to the same data, can be linked or connected. Furthermore, the situation should be prevented where the value of a sensitive attribute can be derived from the values of further attributes. The anonymized data can be evaluated for a large number of medical applications and medical devices without it being possible to draw conclusions about the identity of the patient or people on whose personal data the anonymized data contents are based.

A conventional method for the anonymization of patient data is based on what is known as k-anonymity. K-anonymity is a formal criterion for assessing the anonymity of aggregated data. Different attributes of a data set are firstly divided into non-sensitive and sensitive attributes. The sensitive attributes comprise information in respect of personal data, for example in respect of an illness, of the respective patient. Sensitive attributes are items of information relating to a person that are deserving of protection. The non-sensitive attributes comprise general personal features of the person, such as the age and/or the gender of the respective person. The non-sensitive attributes can for their part be divided into identifiers and quasi-identifiers. An identifier is suitable on its own for uniquely identifying a particular person or a particular patient. In contrast, the quasi-identifiers in combination with other data within the data set, possibly using further datasets, are capable of identifying the relevant patient. The aim of k anonymization is to change a number of datasets in such a way that they are indistinguishable. For this, direct identifiers are removed or concealed (for example name or patient ID replaced by pseudonyms) and quasi-identifiers are changed or concealed in such a way that a dataset may not be emphasized (for example very young or very old people allocated to an interval instead of mentioning the specific age). The resulting dataset is referred to as k-anonymous if each data point remains indistinguishable from at least k−1 further data points. The anonymity of the data is achieved in that no clear allocation is possible between sensitive attribute values and individual data points of people within the group. To carry out an anonymization of a database content, which comprises a large number of patient datasets pertaining to a project, it is conventionally necessary to undertake laborious data preprocessing of the total database content to be anonymized in advance of the anonymization in order to obtain suitable generalization limits for the quasi-identifiers of the patient datasets. This kind of data preprocessing of the database content is impossible, however, if data is continuously being generated, for example owing to a continuous data stream of generated sensor data. If the database content is too great, preprocessing is very often practically unfeasible. In many applications the database content of a project data source comprises many terabytes in respect of a particular project. This is compounded by the fact that the majority of systems used by medical institutes allow only a relatively slow exchange of data. In many medical institutes, for example hospitals, what are known as PACS (Picture Archiving and Communication System) systems are used. These systems comprise, in particular, picture archiving and communication systems, which are also suitable for acquiring and exchanging digital image data.

SUMMARY

Owing to the existing very high data volumes and the limited data transfer speeds of conventional database systems data preprocessing for obtaining anonymization and obfuscation parameters is therefore very time-consuming or practically unfeasible and in many applications even impossible.

It is therefore an object of one or more example embodiments of the present invention to provide a method and a system, which allow existing patient datasets to be efficiently anonymized.

This object is inventively achieved by a computer-implemented method with the features disclosed in accordance with one or more example embodiments and by a corresponding system with the features according to one or more example embodiments.

One or more example embodiments of the present invention accordingly provide a computer-implemented method for providing anonymized patient datasets, having the following steps:

analyzing statistical population data for ascertaining obfuscation parameters, and anonymizing patient datasets, which as attributes contain quasi-identifiers in that the quasi-identifiers of the patient datasets are obfuscated via or based on the ascertained obfuscation parameters for generating the anonymized patient datasets.

One advantage of the inventive computer-implemented method consists in that for ascertaining the obfuscation parameters, no data preprocessing of database contents of a project data source is necessary, instead it is possible to access available statistical databases for this purpose. Obfuscation parameters can be efficiently ascertained hereby without this being prevented by technical limitations of conventional PACS systems. The patient datasets can be anonymized in this way at a much higher speed even when fewer calculations resources are used. The computer-implemented method is thus much faster than conventional anonymization methods and also requires the use of fewer resources, in particular fewer calculation and storage resources. Cybersecurity and data protection aspects also play a part since the patient data is less exposed and less processed.

In one possible embodiment of the inventive computer-implemented method, a quasi-identifier of a patient dataset is obfuscated in that a value of the quasi-identifier is generalized to a generalization interval incorporating it.

In a further possible embodiment of the inventive computer-implemented method, a quasi-identifier of a patient dataset is obfuscated in that one or more digit(s) of the value of the quasi-identifier are at least partially deleted or masked.

In a further possible embodiment of the inventive computer-implemented method, a quasi-identifier of a patient dataset is obfuscated in that the value of the quasi-identifier is changed in an arithmetic or logic operation by a change value. In one possible implementation, the change value can be formed by a random value.

In a further possible embodiment of the inventive computer-implemented method, an obfuscation parameter ascertained by analysis of the statistical population data indicates a spread of a generalization interval for generalization of a quasi-identifier.

In a further possible embodiment of the inventive computer-implemented method, an obfuscation parameter ascertained by analysis of the statistical population data indicates a number and/or a position of digits of a value of the quasi-identifier to be deleted or masked.

In a further possible embodiment of the inventive computer-implemented method, an obfuscation parameter ascertained by analysis of the statistical population data indicates a change value for changing the value of the quasi-identifier.

In one possible embodiment of the inventive computer-implemented method, the patient datasets have different attributes. In one possible embodiment, these attributes comprise identifiers, quasi-identifiers and sensitive attributes. The identifiers are suitable on their own for uniquely identifying the respective patient. In contrast, the quasi-identifiers are only suitable in combination with further data for uniquely identifying the respective patient. The sensitive attributes comprise personal data of the respective patient deserving protection.

In a further possible embodiment of the inventive computer-implemented method, the identifiers contained in the patient datasets are automatically deleted or masked when anonymizing patient datasets.

This can already guarantee a certain level of data security.

In a further possible embodiment of the inventive computer-implemented method, the patient datasets are read from a project data source. The project data source can have a central database or be a distributed database.

In a further possible embodiment of the inventive computer-implemented method, the patient datasets are generated in real-time automatically on the basis of sensor data.

In a further possible embodiment of the inventive computer-implemented method, the patient datasets read from the project data source and/or the patient datasets generated on the basis of sensor data, as a data stream, are obfuscated continuously for their anonymization via or based on the ascertained obfuscation parameters for generating anonymized patient datasets. The anonymized patient datasets generated in the process are preferably stored for further evaluation in an anonymous database.

In a further possible embodiment of the inventive computer-implemented method, the anonymized patient datasets form clusters with a cluster size in which all obfuscated quasi-identifiers are identical.

In a further possible embodiment of the inventive computer-implemented method, on the basis of statistical population data, which is read from one or more statistical database(s), a population expected value is calculated, which for a population of people within a catchment area of a project indicates the number of those people which satisfies the quasi-identifiers of the anonymized patient datasets obfuscated in accordance with an obfuscation option.

In a further possible embodiment of the inventive computer-implemented method, the quasi-identifiers of the patient datasets are obfuscated via or based on the obfuscation parameters in such a way that the calculated population expected value is greater than a selectable cluster size of clusters within the anonymized patient dataset.

In a further possible embodiment of the inventive computer-implemented method, the anonymized patient datasets stored in the anonymous database are used as training data for training an artificial intelligence module, in particular for training an artificial neural network.

In a further possible embodiment of the inventive computer-implemented method, as a function of the anonymized patient datasets stored in the anonymous database, device parameters of medical devices for examining patients are automatically set.

In a further possible embodiment of the inventive computer-implemented method, attributes of the patient datasets of a patient are detected at least partially by sensors.

In a further possible embodiment of the inventive computer-implemented method, the attributes of a patient dataset comprise text data, audio data and/or image data.

The inventive computer-implemented method can be carried out by a corresponding program, which is stored in a computer program product or a computer-readable storage medium or is transferred by a data carrier signal and is read out for execution by a processor of a data processing unit.

In accordance with a further aspect, one or more example embodiments of the present invention provide a system for providing anonymized patient data.

One or more example embodiments of the present invention therefore achieve a system for providing anonymized patient data, having a data processing unit, which is capable of analyzing population data for ascertaining obfuscation parameters and for anonymizing the patient datasets read from a project data source for generating anonymized patient datasets in that quasi-identifiers of the read-out patient datasets are obfuscated via or based on the ascertained obfuscation parameters.

BRIEF DESCRIPTION OF THE DRAWINGS

The present invention will be explained in greater detail below with reference to exemplary embodiments, which are illustrated in the accompanying figures.

The accompanying figures are annexed to enable a better understanding of the present invention and form part of the present disclosure. The drawings illustrate embodiments of the present invention and together with the description are intended to describe the principles of the present invention in more detail. Other embodiments of the present invention and many of the intended advantages of the present invention will become clearly discernible by way of the description made in relation to the drawings. Furthermore, identical reference numerals designate identical or similar parts.

Figure 1:
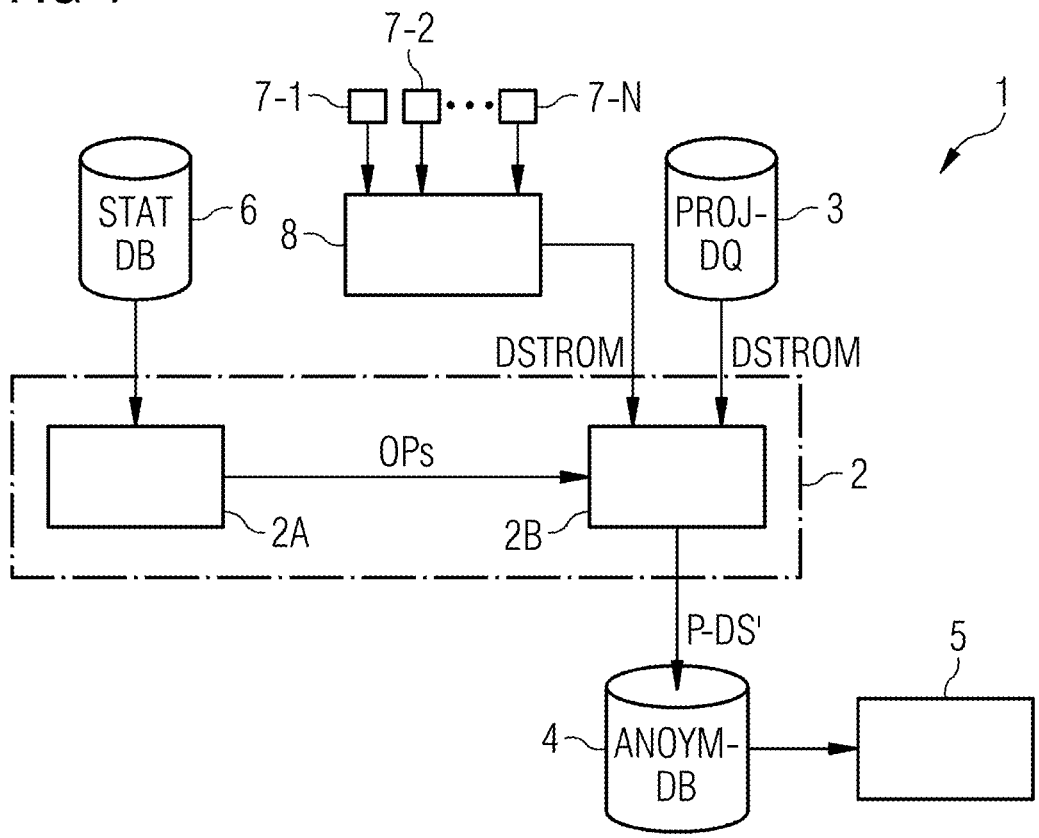

The numbering of method steps is intended to facilitate understanding and is not intended, unless the opposite is explicitly stated or is implicitly clear, to be interpreted in such a way that the designated steps have to be carried out in accordance with the numbering of their reference numerals. Similarly, some or even all of the method steps can be carried out simultaneously, in an overlapping manner or can be executed consecutively.

Figure 2:
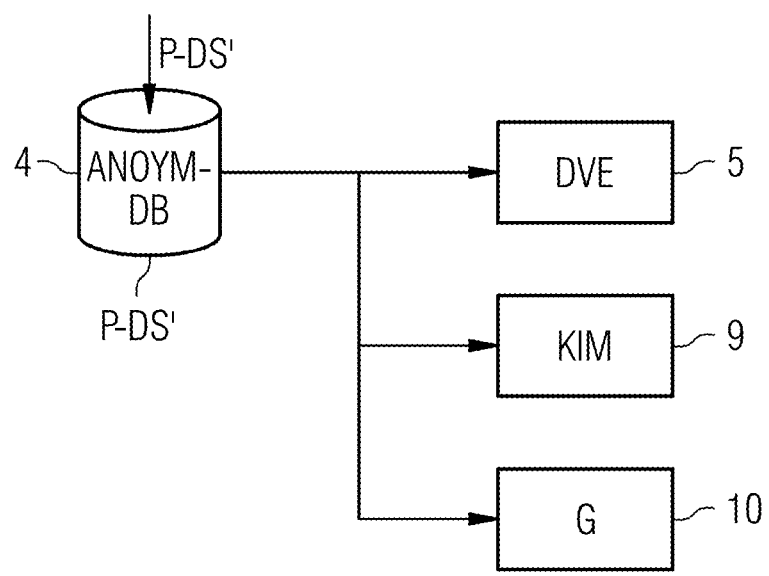

FIG. 1 shows a block diagram to illustrate one possible embodiment of an inventive system for providing anonymized patient data;

FIG. 2 schematically shows possible application examples, which use the patient data anonymized by the inventive system;

FIG. 3 shows a flowchart to illustrate one exemplary embodiment of an inventive computer-implemented method for providing anonymized patient datasets; and FIG. 4 schematically shows a table with patient datasets for explaining the mode of operation of the inventive computer-implemented method and of the inventive system for providing anonymized patient data.

DETAILED DESCRIPTION

FIG. 1 shows a block diagram of one possible embodiment of an inventive system 1 for providing anonymized patient data P-DS. The system 1 has a data processing unit 2 with one or more processor(s), as schematically illustrated in FIG. 1. The data processing unit 2 has a first data processing stage 2A, which is configured to analyze population data for ascertaining obfuscation parameters OP. Furthermore, the data processing unit 2 has a second data processing stage 2B, which anonymizes patient datasets P-DS for generating anonymized patient datasets P-DS'. For this, the second data processing stage 2B of the data processing unit 2 uses obfuscation parameters OP, which are generated by the first data processing stage 2A by analysis of the population data. In the exemplary embodiment illustrated in FIG. 1 the patient datasets P-DS to be anonymized can be read from a project data source 3 of the system 1. The project data source 3 can store a large number of different patient datasets P-DS, which pertain to a project, for example a project in respect of a particular medical situation, for example cardiac infarct diseases or prostate enlargements. The patient datasets P-DS are supplied as a data stream DS to the second data processing stage 2B of the data processing unit 2. The second data processing stage 2B anonymizes the supplied patient datasets P-DS in that the quasi-identifiers Q-IDs of the patient datasets P-DS are automatically obfuscated via or based on the ascertained obfuscation parameters OP. In one possible embodiment, the patient datasets P-DS' anonymized in this way can be stored in an anonymous database 4 for further evaluation. For example, the anonymized patient datasets P-DS' can be supplied to a further data processing unit 5 for further analysis and evaluation. The data processing unit 5 can carry out, for example, an analysis of the anonymized patient datasets P-DS' during the course of a further medical study. In order to carry out the anonymization of the patient datasets P-DS, which are read from the project data source 3, obfuscation parameters OP are used, which are ascertained by the first data processing stage 2A of the data processing unit 2 on the basis of statistical population data. For this, the first data processing stage 2A has access to at least one statistical database 6, as illustrated in FIG. 1. This can be a publicly accessible statistical database 6. No data preprocessing of patient datasets P-DS, which are located, for example, in the project data source 3, is thus necessary for ascertaining obfuscation parameters OP. Laborious data preprocessing, as is necessary in conventional methods, is thus dispensed with in the inventive system 1, as is illustrated in FIG. 1. The second data processing stage 2B, which undertakes the actual analyzing of the patient datasets P-DS, processes a data stream DS, which is generated either by reading from patient datasets P-DS from the project data source 3, or alternatively, is produced also on the basis of sensor data. In the exemplary embodiment illustrated in FIG. 1, different sensors 7-1, 7-2, ... 7-$n$ generate sensor data in respect of possible attributes of a patient. On the basis of the sensor data, a data processing unit 8 generates in real-time patient datasets P-DS, which are supplied as a data stream DS to the second data processing stage 2B of the data processing unit 2 of the system 1, as is schematically illustrated in FIG. 1.

FIG. 4 schematically shows in tabular form a large number of patient datasets P-DS, which are stored, for example, in a project data source 3. The project data source 3 can be a central database of a medical institution or also be formed by a distributed database. A project comprises a very high number of different patient datasets P-DS. A project preferably relates to a particular medical topic or a particular medical situation. The patient datasets P-DS can be generated by different medical organization units, for example hospitals, research laboratories or research institutes. Each patient dataset P-DS comprises different attributes. A patient dataset P-DS comprises, as illustrated in FIG. 4, an identifier ID, which on its own is suitable for uniquely identifying the respective patient. An example of an identifier ID is, for example, the name of the patient or a unique patient number. In addition, each patient dataset P-DS comprises one or more quasi-identifier(s) Q-IDs, which in each case in combination with further data are suitable for identifying the respective patient. Quasi-identifiers Q-IDs are attributes, which, taken in isolation, do not allow identification of the patient, but in combination with generally accessible data enable a unique allocation. As illustrated in FIG. 4, a patient dataset P-DS comprises m quasi-identifiers Q-IDs. Examples of quasi-identifiers Q-IDs are the gender of the patient (male/female) and the age of the patient as well as, for example, a zip code PLZ of the address of the patient. In addition to the quasi-identifiers Q-IDs, each patient dataset P-DS contains sensitive attributes, which comprise personal data of the respective patient. Sensitive attributes comprise personal information, particularly that deserving protection, such as illnesses of the patient, for example influenza or a cancerous disease.

The data processing stage 2B of the data processing unit 2 anonymizes a patient dataset P-DS in that its quasi-identifiers Q-IDs are obfuscated or concealed via or based on ascertained obfuscation parameters OP for generating the correspondingly anonymized patient dataset P-DS'. The obfuscation can take place in different ways depending on the type of quasi-identifier Q-ID. In one possible embodiment a quasi-identifier Q-ID of a patient dataset P-DS can, for example, be obfuscated in that its value is generalized to a generalization interval incorporating it. If, for example, the age of a patient is 35, the value of this quasi-identifier Q-ID can be generalized by an interval, which lies between 30 and 40 years. The range of this generalization interval is thus ten years. The spread or value range of the generalization interval for generalization of a quasi-identifier "age" forms one possible obfuscation parameter OP. For example the age of a target person or a patient who is, for example, 35 years old can also be generalized by a generalization interval, which lies between 30 and 35 years inclusive. Here the obfuscation parameter OP for generalization of the age declaration is only five years. The quasi-identifier "age" on the basis of the patient dataset is thus obfuscated in that a value (age declaration) of the quasi-identifier "age" is generalized to a generalization interval incorporating it and corresponding to an obfuscation parameter OP. Here the obfuscation parameter OP indicates the spread or value range of the generalization interval for generalization of the quasi-identifier "age". With the inventive system 1 the obfuscation parameter OP is ascertained by the first data processing stage 2A of the data processing unit 2 by analyzing statistical population data. This statistical population data can be read from a publicly accessible statistical database 6.

In a further possible embodiment, a quasi-identifier Q-ID of a patient dataset P-DS is obfuscated in that one or more digit(s) of a value of the quasi-identifier Q-ID is/are at least partially deleted or masked. If the quasi-identifier Q-ID consists, for example, of a five-digit zip code PLZ, for example 1, 2, 3 or 4 digits of the zip code PLZ can be deleted or masked in order to partially conceal or obfuscate them. For example the zip code PLZ "80333" of the patient "Charles" can be obfuscated to "8033*" or "803" or "80*" or "8****". Furthermore, the obfuscation parameters OP can also indicate which position or digit position is obfuscated. Typically an obfuscation of a lower digit position results in a lower obfuscation than the obfuscation of a higher digit position. If for example only the last digit of a zip code PLZ is obfuscated, the extent of the concealment is lower than if, for example, the first digit of a zip code PLZ is deleted or masked.

In a further possible embodiment, a quasi-identifier Q-ID of a patient dataset P-DS is obfuscated in that the value of the quasi-identifier Q-ID is changed by a change value. This change value can also be a random value.

Different techniques can be used for obfuscation. In an aggregation-based method, individual data points or data fields of the original patient datasets can be aggregated to form groups, making a reidentification and a determination or reliable estimate of attribute values of individual people or patients difficult.

In random-based obfuscation methods, individual attributes of a patient dataset can be changed in a random-based manner in such a way that a reidentification and reliable estimate of attribute values of individual patients is made difficult.

Furthermore, synthesis-based obfuscation methods can also be used. Firstly a statistical model of the source data is formed. On the basis of this model new synthetic data is subsequently generated, which optimally replicates the source data, but no longer has any personal reference to the respective patient.

The anonymization of the patient datasets by the second stage 2B of the data processing unit 2 can include both a static anonymization as well as a dynamic anonymization. With the dynamic anonymization a continuous data stream DS is anonymized in accordance with particular criteria. With the static anonymization a fully known dataset can be anonymized in accordance with previously defined criteria.

An interactive anonymization is also possible. For example, a request defined by a user for an existing database table can be anonymized on a noise basis.

For anonymizing the patient datasets P-DS by way of the second data processing stage 2B of the data processing unit 2 preferably all unique identifiers ID contained in the supplied patient datasets P-DS are automatically deleted or masked. The additionally existing quasi-identifiers Q-IDs are automatically obfuscated or concealed with the aid of ascertained associated obfuscation parameters OP. Depending on the type of quasi-identifier Q-ID this can take place in different ways according to the ascertained associated obfuscation parameter OP. The patient datasets P-DS read from the project data source 3 and/or the patient datasets P-DS generated on the basis of sensor data, as the data stream DS, are obfuscated for their anonymization continuously via or based on the ascertained obfuscation parameters OP for generating anonymized patient datasets P-DS', as schematically illustrated in FIG. 1. The anonymized patient datasets P-DS' are preferably stored in an anonymous database 4 for further evaluation and analysis.

The analyzed patient datasets P-DS form clusters C with a cluster size K in which all obfuscated quasi-identifiers Q-IDs are identical. On the basis of static population data, which is read from the statistical database 6, in one possible embodiment a population expected value E can be calculated by the data processing stage 2A. For a population of people within a catchment area of the project, this population expected value E indicates the number of those people which satisfies the quasi-identifiers Q-IDs of the anonymized patient datasets P-DS' obfuscated in accordance with an obfuscation option. The quasi-identifiers Q-IDs of the patient datasets are preferably obfuscated via or based on the obfuscation parameters OP in such a way that the calculated population expected value E is greater than a selectable cluster size K of clusters C within the anonymized patient datasets P-DS'.

The anonymized patient datasets P-DS' stored in the anonymous database 4 can be used for different applications. For example, they can be used by a further data processing unit 5 for medical studies. For this, the stored anonymized patient datasets P-DS' can be evaluated further with additional anonymized data.

FIG. 2 schematically shows possible uses of the anonymized patient datasets P-DS' stored in the anonymized database 4. The anonymized patient datasets P-DS' can be used in one possible embodiment as training data for training an artificial intelligence module (KIM) 9. The artificial intelligence module 9 can subsequently be used for medical diagnosis on the basis of further anonymized patient datasets. Furthermore, the anonymized patient datasets P-DS' can also be used for setting device parameters of medical devices 10, which serve for examining patients or samples. Furthermore, the anonymized patient datasets P-DS'can also be used for ascertaining a medical diagnosis, in particular the diagnosis can be carried out outside of the information-technical infrastructure of the hospital due to the use of the anonymized patient datasets P-DS'.

Attributes of the patient datasets, as are illustrated in tabular form in FIG. 4, are at least partially detected by sensors in one possible embodiment of the inventive system 1. For example, identifiers ID of a patient can be read from an identifier or identification of the patient with the aid of a reading unit of the system 1. For example, the identifier ID of a patient is read by the reading unit from a chipcard or health card of the patient, which the patient carries with them. The patient can optionally also carry wearables, which measure and monitor body functions directly, and transfer the patient data. Furthermore, the identifier ID can be read, for example, from an RFID tag.

Quasi-identifiers Q-IDs of a patient can also be detected by sensors or with the aid of a reading unit and be stored as a quasi-identifier Q-ID in the corresponding patient dataset P-DS of the patient. The attributes of a patient dataset P-DS, in other words the identifiers ID, quasi-identifiers Q-IDs and the sensitive attributes, can also comprise audio data and/or image data in addition to text data. The audio data and image data is, for example, sensor data, which is relevant to a particular medical situation, which is examined in the project. For example, the audio data heart sounds can be examined for examining the medical situation of a cardiac infarct. Further examples are, for example, EKG data and the like. In addition to audio data, image data can also form attributes, which are generated during the course of a radiological examination. This image data comprises, for example, CT data or X-ray data of the patient. Furthermore, for example biometric data of a patient can also be evaluated as identifiers ID for identifying the patient. For example, fingerprint data forms image data, which can be used as unique identifiers IDs of a patient. Data detected by sensors, for example image data, can also be evaluated in a data processing process in order to automatically ascertain quasi-identifiers Q-IDs of the relevant person. For example, from a facial image of the patient it is possible to ascertain their gender. Typical examples of quasi-identifiers Q-IDs are, for example, the age, weight, gender or blood group, type of examination or examination date of the patient. These quasi-identifiers Q-IDs are obfuscated with the aid of the obfuscation parameters OP to prevent a back-identification or reidentification of the patient. This occurs with the aid of obfuscation parameters OP, which are ascertained on the basis of statistical population data.

FIG. 3 shows a flowchart to illustrate one possible embodiment of an inventive computer-implemented method for providing anonymized patient datasets P-DS'. In the schematic flowchart the computer-implemented method substantially comprises two main steps S1, S2.

In a first step S1 statistical population data is analyzed for ascertaining obfuscation parameters OP. For example, statistical population data is read from a statistical database 6 and analyzed in order to obtain obfuscation parameters OP therefrom. For example, an obfuscation parameter OP can indicate the range or spread of a generalization interval for generalization of the quasi-identifier "age". The obfuscation parameter OP indicates, for example, that the spread comprises ten years, five years or also just three years.

In a further step S2, patient datasets P-DS, which contain quasi-identifiers Q-IDs as attributes, are anonymized in that the quasi-identifiers Q-IDs of the patient datasets P-DS are obfuscated or concealed via or based on the obfuscation parameters OP ascertained in step S1 for generating the anonymized patient datasets P-DS'. For example, an age declaration of a patient can be generalized within their patient dataset P-DS in that, instead of the exact age declaration, only the corresponding age interval is disclosed. For anonymizing the patient datasets P-DS in step S2 the quasi-identifiers Q-IDs are obfuscated and the identifiers IDs preferably automatically deleted or completely masked.

The anonymized patient datasets P-DS' generated in step S2 are preferably stored in a corresponding anonymous database 4 for further evaluation and use. For example, the stored anonymized patient datasets P-DS' are used for training an artificial neural network KNN (as an example of an artificial intelligence module 9) or for setting device parameters of medical devices, as described in connection with FIG. 2. With the inventive computer-implemented method, as is schematically illustrated in the flowchart of FIG. 3, a k-anonymization procedure can be executed in that the specific properties of the particular database, for example of the database content contained in the project data source 3, are not relevant on their own, but only the parameter distribution of the data values within the total population within the catchment area of the respective project. This parameter distribution can be evaluated for determining the cluster size K of clusters C within the anonymized patient datasets P-DS'. For this, the statistical population data within the catchment area of the project can be read from a statistical database 6 and evaluated by the data processing stage 2A in order to obtain corresponding obfuscation parameters OP. For example, the age distribution of people within the catchment area can be read from a statistical database 6. The age distribution of people within the population is then used for determining a spread of a generalization interval.

In one possible embodiment, a population expected value E can be calculated on the basis of the statistical population data, which is read from the statistical database 6. This indicates as a population of people within the project catchment area the number of those people which actually satisfies the obfuscated quasi-identification Q-IDs of the anonymized patient datasets P-DS' in accordance with an obfuscation option. The obfuscation option comprises a combination of obfuscations in respect of the different quasi-identifiers Q-IDs.

This will be explained in more detail below using a simple example. For example, the catchment area of a particular medical institution, for example a hospital, is known. Furthermore, for example the catchment area in respect of a particular area for a particular project can comprise an area in which, for example, 5 million people live. With a particular medical condition or a particular medical situation, the incidence value for men (who form half of the population) in a predefined age range, for example, is 5 in 100,000. The age range comprises for example 5% of the people living in the relevant area. In this simple example the expected value E of the patients in the corresponding cluster C is (generalized age male):

$$E \text{ total} = 5{,}000{,}000 \cdot \frac{1}{2} \cdot \frac{5}{100{,}000} \cdot \frac{5}{100} = 6.25$$

In this simple example the number A of people in the catchment area of the project is 5 million, with half of the population satisfying the attribute male, the incidence value is $$\frac{5}{100{,}000}$$

and the relevant age range is 5% of the population.

In general, the total population expected value E can be calculated from the number A of people in the catchment area multiplied by the product of the different expected values E in respect of the different attributes of the patient dataset P-DS.

The population expected value E calculated in this way is preferably compared with the cluster size K of clusters C within the anonymized patient datasets P-DS. The obfuscation or concealment via or based on the obfuscation parameters OP has to take place in such a way that the calculated population expected value $E_{total}$ is always greater than the selectable cluster size K of the cluster C within the anonymized table or database.

The quasi-identifiers are thus preferably obfuscated in the manner where the following applies:

$$E_{total} > \rho * K$$

where ρ is a predefined constant (parameter of the system) where ρ≥1.

Where $E_{total}$ is the total expected value and K the cluster size or the extent of the equivalence class.

Different obfuscation techniques with suitable obfuscation parameters OP can be used in the inventive method, with the obfuscation parameters OP always being derived by analysis of statistical population data, which is readily available in statistical databases 6. The size of the clusters C within the anonymized patient datasets P-DS' is set as a function of the calculated statistical expected values $E_{total}$.

The computer-implemented method allows a k-anonymization to be carried out without data preprocessing of the data content of the project data source 3 having to be executed. The anonymization process is significantly simplified and accelerated as a result. Furthermore, the anonymization can also be carried out with a continuous data stream DS of patient datasets P-DS. The anonymization takes place efficiently and in a resource-saving manner on the basis of publicly available statistical population data, which can be read from at least one statistical database 6 via the Cloud or the Internet with short access time. The statistical population data comprises, in particular, static distributions within a population in respect of one or more attribute(s).

In one possible embodiment, the obfuscation parameters OPs are ascertained for analysis of the statistical population data before the actual anonymization in step S2 of the patient datasets P-DS. In a further possible embodiment, the obfuscation parameters OPs can also be dynamically adjusted in the background during the anonymization process in step S2 as soon as the statistical distributions of the relevant parameters in the statistical database 6 also change. Depending on the application, back-couplings, for example of medical devices in which correspondingly anonymized patient datasets P-DS' have also been set, can also be used to adjust the obfuscation parameters OP.

With the inventive system the anonymized patient datasets P-DS' can be made publicly accessible without the data of all examination studies within the project already being available. The inventive system is capable of also processing a continuous data stream DS of patient datasets P-DS, which are generated in real-time, for example, on the basis of sensor data or read data or are read from a database. The inventive method and system 1 is suitable for efficiently anonymizing any patient datasets P-DS with any number of different attributes and thus providing the basis for further evaluations of the studies. Furthermore, the anonymized patient datasets P-DS' can be used as training data or for setting device parameters. The obfuscation parameters OP can be ascertained in advance of the anonymization or also parallel in the background during the continuous anonymization. One advantage of the inventive method thus also consists in that the obfuscation parameters OPs can be ascertained or updated in the background parallel to the anonymization of the patient datasets P-DS. In one possible embodiment, the inventive system 1 is thus also real-time-capable, in other words patient datasets P-DS generated in real-time, which also contain sensor data as attributes, can be obfuscated in real-time for generating anonymized patient datasets P-DS'.

The inventive method can be used in many ways for a wide variety of different applications. The embodiments illustrated in the different figures contain features, which can be combined with each other in the further embodiments. The inventive computer-implemented method and the inventive system 1 for providing anonymized patient datasets P-DS' is not limited to the exemplary embodiments illustrated in FIGS. 1 to 4. Further forms of application and embodiments are possible. For example, the anonymized patient datasets P-DS' can also be rewritten in the project data source 3 as anonymized in a correspondingly characterized manner.

The anonymized patient datasets P-DS' can also be displayed via user interfaces, for example a Graphical User Interface GUI, for a user, for example a project manager of the corresponding medical research project. In one possible embodiment, the obfuscation parameters OPs used in the process are also displayed on a display unit via a user interface of this kind and can optionally be interactively adjusted further.

In a further possible embodiment, the obfuscation parameters OPs are also adapted on the basis of a predefined or input security category SK. Highly sensitive data is obfuscated or concealed to a greater extent than less sensitive patient datasets P-DS. In this embodiment, the obfuscation parameters OP ascertained by analysis of the statistical population data are also adapted or readjusted as a function of security categories SK.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been illustrated and described in more detail on the basis of a preferred exemplary embodiment, the present invention is not limited by the disclosed examples and other variations can be derived herefrom by the person skilled in the art without leaving the scope of protection of the present invention.

What is claimed is:

1. A computer-implemented method for providing anonymized patient datasets, the computer-implemented method comprising:
analyzing statistical population data to ascertain obfuscation parameters; and
anonymizing patient datasets that include quasi-identifiers as attributes, the anonymizing including obfuscating the quasi-identifiers based on the obfuscation parameters to generate the anonymized patient datasets; wherein the patient datasets are read from a project data source, the statistical population data is read from at least one statistical database, and each patient dataset of the patient datasets corresponds to a project and the statistical population data for the project is for a catchment area of the project.

2. The computer-implemented method as claimed in claim 1, wherein the obfuscating comprises:

obfuscating a quasi-identifier of a patient dataset by generalizing a value of the quasi-identifier to a generalization interval incorporating the value of the quasi-identifier, at least partially deleting or masking one or more digits of the value of the quasi-identifier, or changing the value of the quasi-identifier by a change value in an arithmetic or logic operation.

3. The computer-implemented method as claimed in claim 1, wherein an obfuscation parameter ascertained by analyzing the statistical population data indicates a spread of a generalization interval for generalization of a quasi-identifier, at least one of a number or position of digits to be deleted from a value of the quasi-identifier, or a change value for changing the value of the quasi-identifier.

4. The computer-implemented method as claimed in claim 1, wherein the patient datasets include different attributes, and wherein the different attributes include identifiers uniquely identifying a respective patient, the quasi-identifiers, which in combination with further available data identify the respective patient, and sensitive attributes, which include personal data of the respective patient.

5. The computer-implemented method as claimed in claim 4, wherein the anonymizing patient datasets comprises:

automatically deleting or masking the identifiers contained in the patient datasets.

6. The computer-implemented method as claimed in claim 1, further comprising:

reading the patient datasets from the project data source; and generating the patient datasets in real-time based on sensor data detected by sensors.

7. The computer-implemented method as claimed in claim 6, further comprising:

continuously obfuscating the patient datasets as a data stream, based on the obfuscation parameters, to generate the anonymized patient datasets; and storing the anonymized patient datasets in an anonymous database.

8. The computer-implemented method as claimed in claim 1, wherein the anonymized patient datasets form clusters with a cluster size in which all obfuscated quasi-identifiers are identical.

9. The computer-implemented method as claimed in claim 1, further comprising:

calculating a population expected value based on the statistical population data, wherein the population expected value indicates, for a population of people within the catchment area of the project, a number of people satisfying the quasi-identifiers of the anonymized patient datasets obfuscated in accordance with an obfuscation option.

10. A computer-implemented method for providing anonymized patient datasets, the computer-implemented method comprising:

analyzing statistical population data to ascertain obfuscation parameters;

calculating a population expected value based on the statistical population data; and anonymizing patient datasets that include quasi-identifiers as attributes, the anonymizing including obfuscating the quasi-identifiers based on the obfuscation parameters to generate the anonymized patient datasets, wherein the statistical population data is read from at least one statistical database, the population expected value indicates, for a population of people within a catchment area of a project, a number of people satisfying the quasi-identifiers of the anonymized patient datasets obfuscated in accordance with an obfuscation option, and the quasi-identifiers of the patient datasets are obfuscated based on the obfuscation parameters, such that the population expected value is greater than a selectable cluster size of clusters within the anonymized patient dataset.

11. The computer-implemented method as claimed in claim 7, further comprising:

training an artificial intelligence module based on the anonymized patient datasets stored in the anonymous database.

12. The computer-implemented method as claimed in claim 7, further comprising at least one of:

setting device parameters of medical devices for examining patients as a function of the anonymized patient datasets stored in the anonymous database, or automatically creating at least one medical diagnosis relating to patients based on the anonymized patient datasets stored in the anonymous database.

13. The computer-implemented method as claimed in claim 1, wherein attributes of a patient dataset of a patient are at least partially detected by sensors or read from an identifier.

14. The computer-implemented method as claimed in claim 1, wherein attributes of a patient dataset include at least one of text data, audio data or image data.

15. A non-transitory computer program product including computer-executable commands that, when executed by a computer, cause the computer to perform the method as claimed in claim 1.

16. A non-transitory computer-readable storage medium, comprising computer-executable commands that, when executed by a computer, cause the computer to perform the method as claimed in claim 1.

17. A system for providing anonymized patient datasets, the system comprising:

at least one processor; and a memory storing computer-executable instructions that, when executed by the at least one processor, cause the system to analyze statistical population data to ascertain obfuscation parameters, and anonymize patient datasets read from a project data source to generate the anonymized patient datasets by obfuscating quasi-identifiers of the patient datasets based on the obfuscation parameters, wherein the patient datasets are read from a project data source, the statistical population data is read from at least one statistical database, and each patient dataset of the patient datasets corresponds to a project and the statistical population data for the project is for a catchment area of the project.

18. The computer-implemented method as claimed in claim 2,
wherein an obfuscation parameter ascertained by analyzing the statistical population data indicates a spread of the generalization interval for generalization of the quasi-identifier, at least one of a number or position of digits to be deleted from the value of the quasi-identifier, or the change value for changing the value of the quasi-identifier.

19. The computer-implemented method as claimed in claim 11, wherein the artificial intelligence module is an artificial neural network.

20. The computer-implemented method as claimed in claim 2, further comprising:
calculating a population expected value based on the statistical population data, wherein
the population expected value indicates, for a population of people within the catchment area of the project, a number of people satisfying the quasi-identifiers of the anonymized patient datasets obfuscated in accordance with an obfuscation option.

* * * * *